United States Patent [19]
Adamski et al.

[11] Patent Number: 5,529,675
[45] Date of Patent: Jun. 25, 1996

[54] ELECTROSTATIC COALESCER TESTING APPARATUS

[75] Inventors: Robert P. Adamski, Missouri City; Eugene L. Holloway, Richmond; Rodney T. Pennington, Houston, all of Tex.

[73] Assignee: Shell Oil Company, Houston, Tex.

[21] Appl. No.: 357,827

[22] Filed: Dec. 16, 1994

[51] Int. Cl.⁶ .................................................. G01N 27/00
[52] U.S. Cl. ........................ 204/400; 204/666; 204/669; 204/671; 324/453; 324/457; 324/158.1
[58] Field of Search ................................ 204/153.1, 400, 204/409, 302, 304, 305, 307, 308

[56] References Cited

U.S. PATENT DOCUMENTS

| | | | |
|---|---|---|---|
| 2,678,911 | 5/1954 | Chittum | 204/181.9 |
| 2,859,404 | 11/1958 | Crittendon | 324/442 |
| 4,023,096 | 5/1977 | Schmidt | 324/663 |
| 4,134,799 | 1/1979 | Allen et al. | 204/153.1 |

Primary Examiner—John Niebling
Assistant Examiner—William T. Leader
Attorney, Agent, or Firm—Timothy J. Hadlock

[57] ABSTRACT

The invention is an electrostatic coalescer testing apparatus for testing the ability of chemical additives to facilitate electrostatic coalescence of water in a water hydrocarbon-containing mixture. The apparatus includes: (a) a plurality of tubular containers for containing the water-hydrocarbon mixture, each of the tubular containers having one open end and one closed end, and made of a material not substantially electrically conductive; (b) a heating block/electrode having a plurality of tubular recesses therein, each of the tubular recesses for receipt of one of the tubular containers disposed closed-end down, the heating block/electrode comprising of a heat conducting and electrical current conducting material, for conducting heat to the tubular containers, and for applying an electrical potential across the water-hydrocarbon mixture; (c) a mixing blade/electrode member disposed within each of the tubular containers for mixing the water-hydrocarbon mixture with the chemical additive, and for applying an electrical potential to the water-hydrocarbon mixture; (d) a transformer means having two poles for applying an electrical potential to the two electrodes wherein; one pole is connected to the mixing blade/electrode; and one pole is connected to the heating block/electrode.

16 Claims, 4 Drawing Sheets

ELECTROSTATIC COALESCER TESTING APPARATUS

FIELD OF THE INVENTION

The invention relates to a testing apparatus for simulating conditions of an electrostatic coalescer for removal of a water phase from a water-hydrocarbon mixture.

BACKGROUND OF THE INVENTION

Introduction

Electrostatic coalescers are used for crude oil dehydration in both Production and Refining. These devices enhance the coalescence of water droplets by the use of an applied electric field. In a strong electric field, water droplets have an induced dipole and are deformed into an ellipsoidal shape. Attraction between the positive and negative ends of adjacent water droplets is a driving force for coalescence. Distortion of the stabilizing emulsifier film (solids, surfactants, asphaltenes, and other compounds) surrounding the water droplets also assists in droplet coalescence.

Chemical additives, such as demulsifiers and solids-wetting agents, are often used in conjunction with applied electric fields for crude oil dehydration. These additives function to destabilize the emulsifier film surrounding the water droplets. Portable batch electrostatic coalescers are used by chemical vendors to conduct quick screening tests for selecting the best chemical additive package for a given crude oil/brine system. These experiments rank order the relative performance of different additive packages and approximate their performance in commercial-scale electrostatic coalescers.

Known Devices

InterAv markets a commercially available electrostatic coalescer. Petrolite & Betz have built portable electrostatic coalescers in-house. The InterAv device uses an electrode configuration which is susceptible to electrical shorting when the water concentration gets too high, since both electrodes are immersed in the sample. In the InterAv electrostatic coalescer, there is no means for mixing the sample directly in the tube which is used in the electrostatic coalescer. Demulsifier additives for use in electrostatic coalescers are conventional and many varieties of demulsifiers are commercially available from vendors such as Petrolite and Betz.

SUMMARY OF THE INVENTION

We have developed a portable batch electrostatic coalescer along with an oil/water mixing apparatus.

More specifically, the invention relates to an electrostatic coalescer testing apparatus for testing the ability of chemical additives to facilitate electrostatic coalescence of water in a water-hydrocarbon-containing mixture including: (a) two or more tubular containers for containing the water-hydrocarbon mixture, each of the tubular containers (1) having one open end and one closed end, and (2) including a material not substantially electrically conductive; (b) a heating block/electrode having two or more tubular recesses therein, (1) each of the tubular recesses for receipt of one of the tubular containers disposed closed-end down, (2) the heating block/electrode including a heat conducting and electrical current conducting material, (i) for conducting heat to the tubular containers, and (ii) for serving as an electrical ground for the electrical potential placed across the water-hydrocarbon mixture; (c) a mixing blade/electrode member disposed within each of the tubular containers for mixing the water, hydrocarbon, and chemical additives, and (1) for applying an electrical potential to the water-hydrocarbon mixture; (d) a transformer means having two poles for applying an electrical potential to the two electrodes wherein; (1) one pole is connected to the mixing blade/electrode; and (2) one pole is connected to the heating block/electrode.

BRIEF DESCRIPTION OF THE DRAWINGS

Experimental Results

Experimental Results

Experimental Results

Problems Solved (1) Use of one internal and one external electrode to eliminate the possibility of electrical shorting and hydrogen evolution due to water hydrolysis.

(2) Use of variable voltage settings for each sample tube to allow for greater flexibility and efficiency when planning an experimental program using the apparatus.

(3) Use of independent but simultaneous mixing of the 4 sample tubes to allow for greater flexibility and efficiency when planning an experiment.

(4) Use of shielding on apparatus to increase sample viewing safety.

(5) Use of an electrical configuration which will allow for use of both AC and DC (i.e., rectified AC) current to power the electrostatic coalescer.

Uses

The electrostatic coalescer testing apparatus of this invention has several valuable uses in the oil/chemical industry. First, the invention is especially configured to optimize performance of refinery desalters. Specifically, it is useful to optimize the demulsifier treatments in such desalters. In this regard, the electrostatic coalescer can be utilized in both a preventative and curative fashion. That is, the oil feed and water and potential demulsifier additives can be tested in advance of running them in the electrostatic coalescer to determine the best amount and type of demulsifier to be used. In the curative sense, if an emulsion layer in an electrostatic coalescer grows too large and/or unduly increases, samples of that layer can be tested in the testing apparatus to determine a type and/or amount of a demulsifier effective to reduce the size of the emulsion layer. Variations in electrical potential can also be tested in this way.

Second, it is also optionally used to determine the effect of slop oil addition to desalters for determining, e.g., maximum slop oil that may be added or additional demulsifier quantities or types needed when slop oil is added.

Third, the portable batch electrostatic coalescer can be used in new applications where electrostatic coalescers have not traditionally been used. For example, it could be used to determine the feasibility of using strong electric fields for coalescing water droplets in water-washed polymer cements.

DETAILED DESCRIPTION OF THE INVENTION

Overview

The oil/water mixing apparatus prepares emulsion samples in specially made thick walled centrifuge tubes. The tubes are typically glass since this permits visible inspection and prevents any significant electrical conduction. Glass tubes are of sufficient thickness to not break under normal usage with this apparatus. Two millimeters or more of thickness is typically sufficient. The volume of the tubes can vary but the size and shape must match up with the tubular recesses in the heating block/electrode. About 75 ml or more is typical. The centrifuge tubes accept a Nylon plug fitted with a built in mixer-bushing assembly. A separate direct gear drive mechanism converts a single mixer spindle to one that accommodates four tubes simultaneously. The direct gear drive mechanism is optionally constructed to mount on, for example, a standard commercial blender base, e.g., a Waring brand blender. Centrifuge tubes are inverted into a positioning sleeve and then locked into place on the drive pin. Mixing speed is, optionally, controlled using a variable transformer connected to the blender motor. The duration of mixing is optionally controlled by any conventional electronic device suitable for precision timing of the on/off switching of an electrical appliance. A variety of mixer blade designs and shaft lengths can be attached to the mixer-bushing assembly inside the centrifuge tubes. Typically a 4-fin, 7.5 cm long stainless steel paddle mixer may be used.

Once emulsions of suitable drop size distribution are prepared, the samples are exposed to a strong electric field in the batch electrostatic coalescer. Various geometries can be used to accommodate various pluralities of tubes. In one embodiment, up to four centrifuge tubes can be run at a time. The coalescer testing apparatus uses an AC field. The field is typically at 60 Hz. Alternatively, the coalescer testing apparatus can utilize a DC (i.e., rectified AC) field. Maximum AC operating potential can vary from 0 to about 8,000 volts (RMS). Electric fields across the samples can be independently set since each has its own transformer and variable voltage controller. Separate voltage read-outs are also present. Optionally, an electronic digital timer with automatic power shut-down is used to start and stop an experiment.

Electrical Fields

Electric fields in the batch electrostatic coalescer are generated using the mixing blade inside each centrifuge tube as the energized electrode. The centrifuge tubes are placed inside the slots of an aluminum heat block which functions as the ground electrode. Use of one internal electrode and one external electrode in this way eliminates the possibility of electrical arcing. The aluminum heat block also permits the emulsion samples to be preheated up to temperature which will best emulate the conditions inside an industrial size coalescer. Typically, the heating block is heated to about 250° F. before applying the electrical field. Typically, the maximum controllable temperature of the heating block is about 300° F.

DETAILED DESCRIPTION OF THE DRAWINGS

Figure 1:
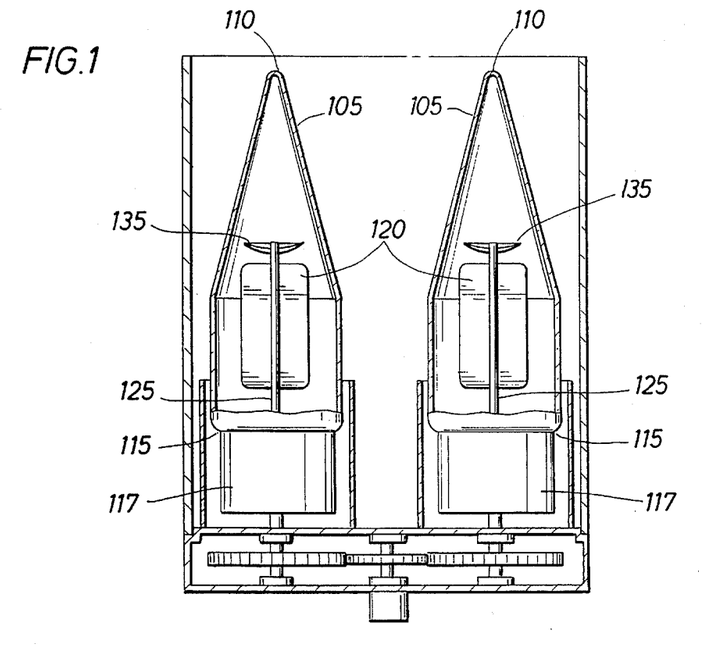
FIG. 1 is a side view of one embodiment of the mixer assembly.

FIG. 1 is a side view of one embodiment of the mixer assembly. Glass tubular containers 105 are in an inverted position, i.e., with closed ends 110 higher than open ends 115. Stopper member 117 is removably/threadably attached to the open end 115 of tubular container 105. Mixing blade/electrodes 120 are made of central shaft member 125 and shearing member 130. Vortex breaker member 135 is fixedly attached on central shaft member 125 "below" (when closed end of container is down) shearing member 130.

Figure 2:
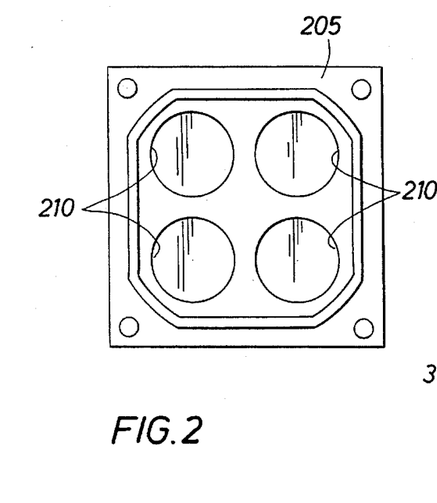
FIG. 2 is a top view of the heating block/electrode in one embodiment.
Figure 3:
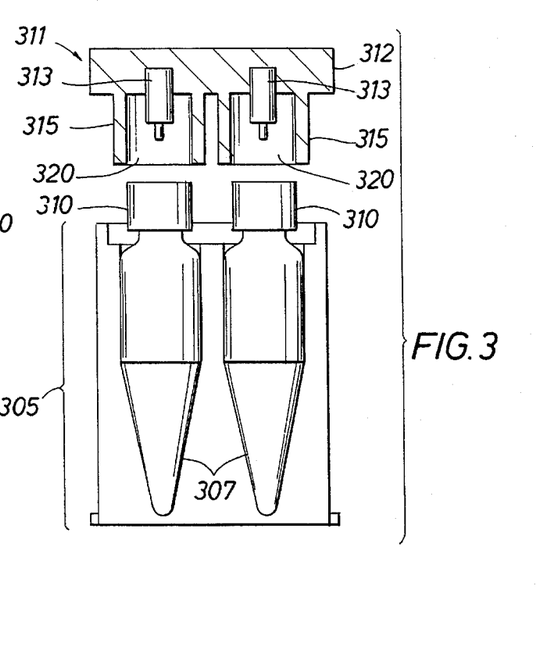
FIG. 3 depicts an exploded side view of the cover member and the tubular containers positioned in the heating block/electrode.

FIG. 2 is a top view of the heating block/electrode in one embodiment. Heating block/electrode 205 has a plurality of tubular recesses 210 therein. The recesses 210 are typically equally spaced from the walls of the heating block/electrode 205. FIG. 3 shows the position of the tubular containers in the tubular recesses.

FIG. 3 depicts an exploded side view of the cover member and tubular containers positioned in the heating block/electrode. Tubular containers 307 of FIG. 3 repose in the tubular recesses 210 of FIG. 2. The closed end of the tubular containers is down and the open end is up. Stopper members 310 are threadably attached to the open end of tubular containers 307.

FIG. 3 also depicts an embodiment of cover member 311. Cover member 311 includes a common plate member 312, electrical connection means 313, and a cylindrical member 315. Electrical connection means 313 and cylindrical members 315 are fixedly attached to common plate member 311. Cylindrical members 315 each have an open bottom portion 320. When in use, cylindrical member 315 surrounds the sides of stopper member 310.

Each electrical connecting means 313 is in electrical contact with one pole of the corresponding transformer means (shown in FIG. 4, #425) and in electrical contact with the corresponding central shaft member (shown in FIG. 1, #125). The other pole of the transformer means is in electrical contact with the heating block/electrode 305 (corresponding to FIG. 2, #205).

Figure 4:
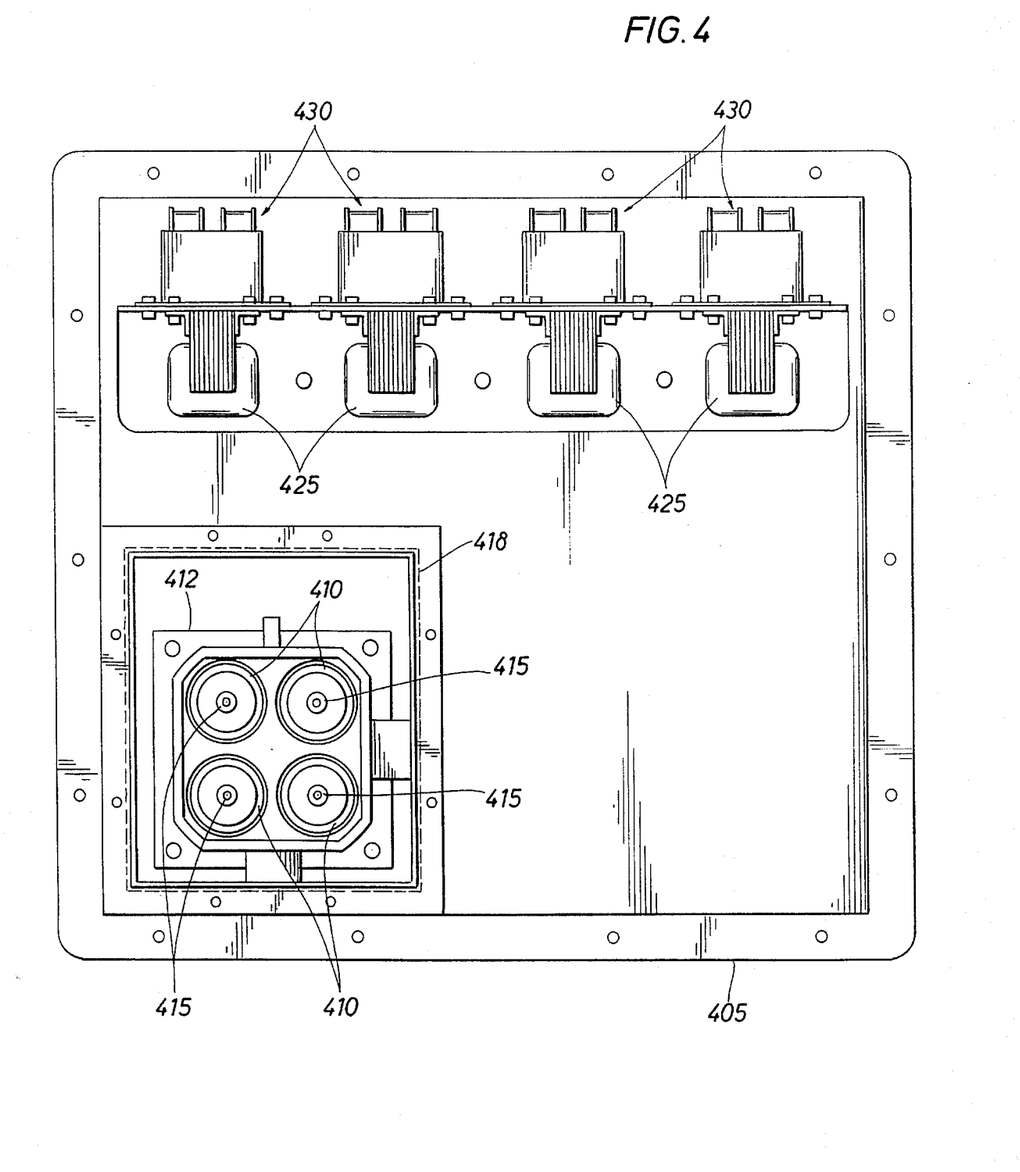
FIG. 4 is a top view of one embodiment of the Aluminum heating block/electrode and depicting an embodiment of the transformer means both located in a common casing.

FIG. 4 is a top view of one embodiment of a common casing containing the Aluminum heating block/electrode and depicting an embodiment of the transformer means. Heating block/electrode 407 is shown in the bottom left corner of FIG. 4. Tubular containers are reposed in tubular recesses 410. Cover member 412 contains electrodes 415. Transformer means 425 are fixedly attached in common casing 405 for attachment of the poles 430 of the transformer means to the heating block electrode 407 and central shaft members.

The dashed line 418 around the circumference of heating block/electrode 407 represents the "footprint" of an explosion-resistant shield removably disposed over the top portion of the heating block/electrode. The explosion-resistant shield can be a rectangular structure composed of a strong but preferably transparent material such as LEXAN® for protecting the operator from glass and chemicals in the event of a glass tube failure while the tube is under pressure. In one embodiment the explosion-resistant shield is only threesided. That is, its back side, the side away from the operator being open since this allows pressure release in the event of explosion and does not endanger the operator.

ILLUSTRATED EMBODIMENTS OF THE INVENTION

Introduction

Three types of experiments were performed to the test the apparatus of the invention. First, the potential effect of slop oil addition to the desalter feed was tested. Second, the relative effectiveness of different demulsifier additives was tested. Third, the amount of demulsifier needed when the crude oil feed blend is changed was tested.

Figure 5A:
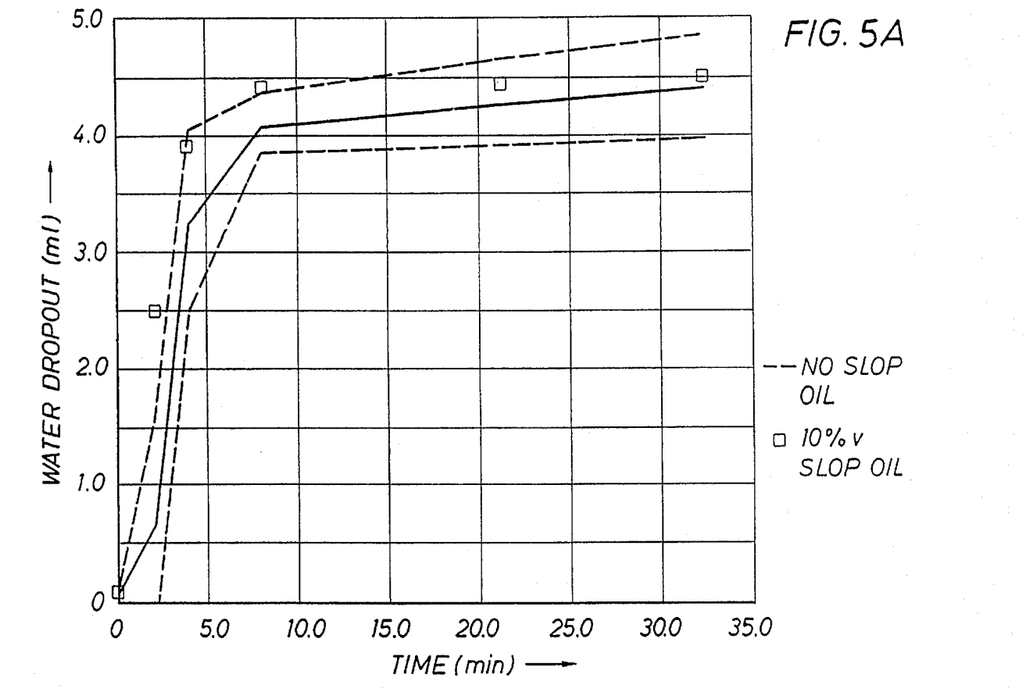
FIG. 5A shows water dropout with time for a mixed crude oil feed to a refinery desalter. The result with no added slop oil is given by the solid curve and the data points indicated by open squares are the result for the mixed crude oil feed with 10% slop oil.

First Illustrative Embodiment: Testing for the Effects of Slop Oil On The Performance of the Electrostatic Coalescer Slop oil generated during refinery turnaround can be rerun through the desalters after the turnaround is completed. In one experimental embodiment the apparatus of the invention was used to determine the effect of such slop oil addition on the coalescence of water-in-crude oil emulsions. Laboratory experiments were conducted using the testing apparatus of the invention to determine the potential impact of rerunning slop oil on desalter performance. As shown in the results and FIG. A discussed below, no negative desalter impact was found at a slop oil addition rate of 10% v basis the mixed crude feed rate.

Experimental Procedure

Oil and Water Samples

Laboratory experiments were conducted using oil and water samples. A mixed crude oil feed sample was dated Jul. 18, 1994. The sample was collected upstream of the desalter and before addition of any demulsifier. A sample of desalter wash water was taken dated May 18, 1994. A pH equal to 8 was measured using an Orion pH Meter.

Slop Oil Preparation

Slop oil which would be produced during the turnaround of a crude oil distillation unit was simulated in the laboratory using the components listed in Table 1. Amounts of each of the components were based on the volumes anticipated during a turnaround. Surfactant "Q" and surfactant "Y" were included in the mixture as shown below since they would be used for cleaning the equipment in a turnaround decontamination. The tradenames are not given since they are not a pertinent factor, since they are constants.

TABLE 1

Components Mixed Together To Generate Slop Oil

| Material | Anticipated Volume* (gal) | Relative Volume % |
|---|---|---|
| Crude Oil Feed | 1,287,500 | 36.5 |
| Straight Run Light Gas Oil | 813,500 | 23.1 |
| Surfactant "Y" (@1% v basis circ. water) | 7,068 | 0.2 |
| Surfactant "Q" (@1% v basis circ. water) | 7,068 | 0.2 |
| Circulation Water** | 706,800 | 20.0 |
| Rinse Water** | 706,800 | 20.0 |

*Estimated volumes of refinery effluent after a distillation unit decontamination.
**DI water was used in laboratory experiments instead of fire water.

The components listed in Table 1 above were added in the proportions shown in Table 1 to a container and vigorously mixed. An oil and aqueous phase quickly separated after mixing was stopped. No emulsion ("rag") layer was detected. However, the aqueous layer initially had a turbid appearance due to entrained oil, but clarified after a longer settling time. The oil phase was used as the slop oil in the laboratory experiments.

Electrostatic Coalescence

A baseline of current desalter operating performance was obtained by running an experiment without slop oil. Samples of crude oil feed were mixed with 12 ppm of demulsifier "G" and were further mixed with desalter wash water at ambient temperature for 2 seconds at 9500 RPM using in-tube paddle mixers (mixing blade/electrodes 120 of FIG. 1).

Total amounts of crude oil feed and desalter wash water were 70.3 ml and 4.7 ml, respectively. The samples were heated to 225° F. for twenty minutes and then exposed to an AC electrical field of 5000 volts. Observations of water dropout were made at cumulative times equal to 2, 4, 8, 16, and 32 minutes of the applied electrical voltage. The above experiment was repeated with slop oil (10% v basis the crude oil) added to the crude oil feed and also mixed with 12 ppm of demulsifer "G".

Results and Discussion

Electrostatic coalescence results are shown in Experimental Results FIG. A. Operating conditions were chosen for the laboratory experiments to give the capability of discerning differences in water dropout rates, if they exist, between samples with and without the slop oil. Trends observed in the laboratory experiments should realistically model the trends that would be observed in a refinery desalter.

Water dropout with time for the mixed crude oil feed to a refinery desalter with no added slop oil is given in Experimental Results FIG. A. Water dropout volumes for crude oil feed containing 10% v slop oil are given by the open squares. The solid line is the average water dropout measured in four duplicate experiments without slop oil, and the dotted lines represent the average water dropout plus or minus two standard deviations. Addition of 10% v slop oil to the mixed crude oil feed had no significant effect on water dropout.

Figure 5B:
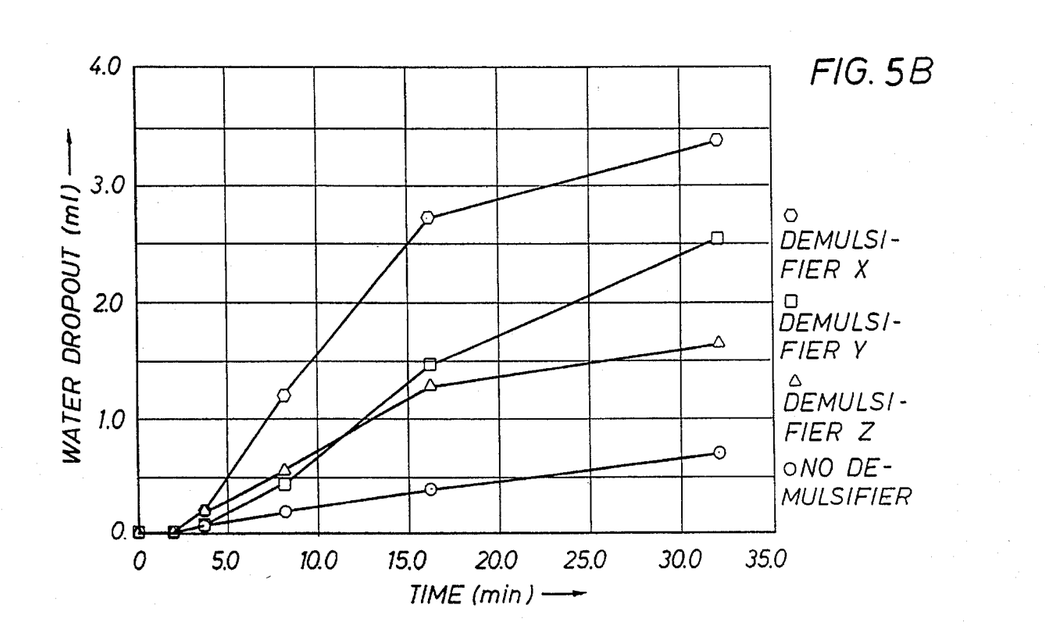
FIG. 5B shows drop out volume of water for different demulsifiers.

Second Illustrative Embodiment: Use of the Electrostatic Coalescer for Evaluating Demulsifier Performance In another experimental embodiment the apparatus of the invention was used to determine the effect of different demulsifiers on the coalescence of water-in-crude oil emulsions. Laboratory experiments were conducted using the testing apparatus of the invention to determine the potential impact of adding different demulsifiers to the feed on refinery desalter performance. As shown in the results and FIG. B discussed below, demulsifier composition X was found to be the most effective under the experimental conditions.

Experimental Procedure

Oil and Water Samples

Crude oil samples were obtained from the Distilling Unit at the Martinez Manufacturing Complex in one gallon epoxy-lined cans. The crude oil samples were collected from a storage tank before the addition of wash water and demulsifiers. The batch of crude oil was collected Jul. 18, 1994. Desalter wash water was also obtained from this location on the same date. This was filtered stripped sour water having a pH between 7.8 and 8.2. The desalter wash water was supplied in one gallon epoxy-lined cans.

Demulsifier Additive

Demulsifier additives were obtained from Petrolite, Betz, and Nalco, which are commercial vendors of such additives to the petrochemical industry. For simplicity and since which vendor's product performed best in these tests is not material to establishing this invention, the different vendor's demulsifiers are labelled Demulsifier X, Demulsifier Y, and Demulsifier Z, where the order of the label does not necessarily correspond with the order the vendors are listed.

Electrostatic Coalescence

Experiments were conducted using the batch electrostatic coalescer testing apparatus of this invention and mixing assembly. Sample preparation involved adding 25 ppm of the primary emulsion breaker additive (i.e., demulsifier additive) to the crude oil and the appropriate amount of a reverse emulsion breaker to the desalter wash water. The primary breakers were delivered from 1% v solutions in toluene, while the reverse breakers were first diluted to 1% v solutions in the desalter wash water and then further diluted with additional desalter wash water.

After sample preparation, 3.6 ml of desalter wash water and 71.4 ml of crude oil were added to the thick-walled centrifuge tubes used in the testing apparatus of the invention and mixing assembly. The tubes were then heated to 180° F. for 20 minutes. In groups of four, the heated centrifuge tubes were inverted onto the mixing adapter and simultaneously mixed for 20 seconds at the "low" blender setting. Each tube had an internal shaft member having attached shearing members (i.e., paddles for mixing). The "low" blender setting corresponded to a mixer speed of approximately 9800 RPM.

The emulsified crude oil samples were removed from the mixing adapter and placed in the heat block of the batch electrostatic coalescer testing apparatus. The tubes were heated to 250° F. for 20 minutes and the water dropout volumes were recorded. This time was designated as time zero. A 3000 volt ac electric field was then applied to the samples in the following time interval sequence: 2 minutes, 2 minutes, 4 minutes, 8 minutes, and 16 minutes. Water dropout volumes were visually measured after each time interval.

Results and Discussion

Electrostatic coalescence results are shown in Experimental Results FIG. B. Operating conditions were chosen for the laboratory experiments to give the capability of discerning differences in water dropout rates, if they exist, between samples with different demulsifier additives and the base line sample with no demulsifier additive. Trends observed in the laboratory experiments should realistically model the trends that would be observed in a refinery desalter. Concentrations given for the primary emulsion breakers are basis the crude oil.

Average water dropout measured for the four desalter additive treatments (X, Y, Z, and No Demulsifier) were evaluated for statistical differences. An analysis of variance procedure (ANOVA) was done which accounted for the differences in the sample tubes used in the experiments. The ANOVA was performed on a time-by-time basis for each of the time intervals in the experiment. A multiple comparison procedure followed the ANOVA to identify which demulsifier package was statistically superior in performance.

Eight sample tubes were used in the experiments and were identified as 1, 2, 3, . . . , 8. The ANOVA model used in the analysis was as follows:

$$\text{Water Dropout}_{ij} = \text{Mean} + \text{Treatment}_i + \text{Tube}_j + \text{Error}$$

This analysis handles the tube effect as an incomplete block.

Table 2 below summarizes the ANOVA results for the significance of the desalter additive treatments. The statistics for Time=0 were not available since all of the measured values were zero.

A Student-Newman-Kuels (SNK) multiple comparison procedure was used after the ANOVA procedure to determine which additive packages were different from the others. The evaluations were done at the 5% level of significance. Table 3 below summarizes the results of this procedure.

Demulsifier X was found to be the best demulsifier package for maximizing water dropout for this oil feed and water feed under the tested conditions. Demulsifier Y came in second, while demulsifier Z was the least effective. All of the demulsifiers performed better than the base line sample with no chemical additives.

TABLE 2

ANOVA Results for the Effects of Desalter Additive Treatments on Water Dropout

| Times (mins.) | Mean Square Error | Additive Package p-Value |
|---|---|---|
| 0 | NA | |
| 2 | 0.000375 | 0.6667 |
| 4 | 0.00975 | 0.2088 |
| 8 | 0.07000 | 0.0138 |
| 16 | <0.0001 | 0.0001 |
| 32 | <0.0001 | 0.0001 |

TABLE 3

Evaluation of Desalter Additive Treatments Using a Student-Newman-Kuels (SNK) Multiple Comparison Procedure

| Time (mins.) | Results |
|---|---|
| 0 | NA |
| 2 | not done since Y = Z = X = T by ANOVA |
| 4 | not done since Y = Z = X = T by ANOVA |
| 8 | T = Y = Z < X . . . so X is superior |
| 16 | T < Z < Y < X . . . so X is superior |
| 32 | T < Z < Y < X . . . so X is superior |

T = No Demulsifier

Figure 5C:
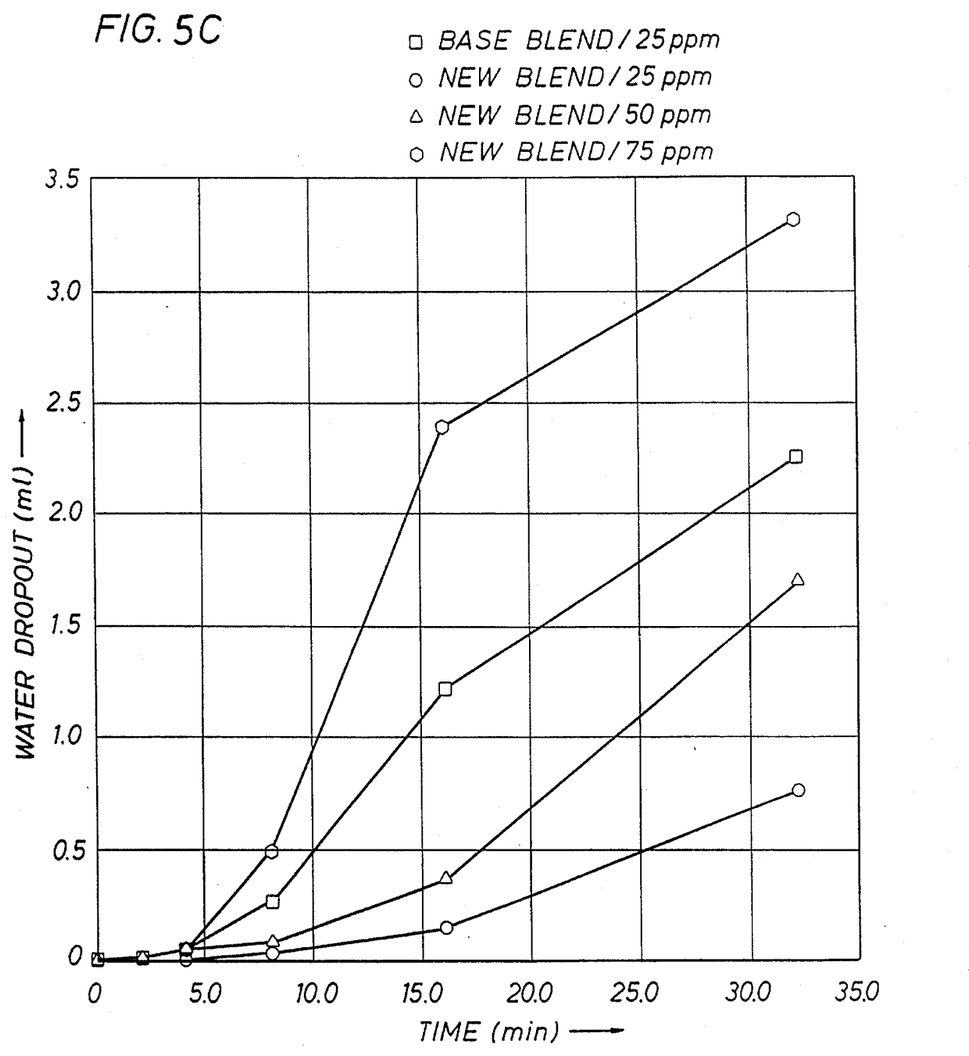
FIG. 5C shows how much demulsifier is needed with a new feed blend to obtain as good a drop out volume of water as with the prior feed blend.

Third Illustrative Embodiment: Test fir Change of Demulsifier Quantity Needed for a New Feed Blend In this Illustrative Embodiment, the same procedure of testing four samples was followed as in the previous Illustrative Embodiments, except as discussed below. The variables changed in this Illustrative Embodiment were the feed oil blend and the demulsifier concentration. The "base blend" sample contains the "old" feed oil blend (67% crude A, 21% crude B, 12% crude C, and 0% crude D) and the amount of demulsifier necessary to obtain the water drop out shown on FIG. C. Each of the other three samples contains the same "new feed oil blend" (57.1% crude A, 17.9% crude B, 10.7% crude C, and 14.3% crude D) and different amounts of the same demulsifier used in the "base blend" sample. The object was to utilize the apparatus of the invention to determine the amount of demulsifier in the "new blend" to obtain as good a water drop out rate as with the "old blend."

The results for this Illustrative Embodiment are shown in FIG. C. One line shows the water drop out curve for the "base feed blend" with 25 ppm of demulsifier. The other curves show water drop out rates for 25 ppm, 50 ppm, and 75 ppm of demulsifier added to the "new feed blend." As shown by FIG. C, the amount of demulsifier needed with the "new feed blend" to obtain the same water drop out is between about two and three times the amount of demulsifier needed with the "base feed blend."

This Illustrative Embodiment shows the device of the invention is useful for determining new demulsifier needs when the feed blend is changed.

What is claimed is:

1. An electrostatic coalescer testing apparatus for testing the ability of chemical additives to facilitate electrostatic coalescence of water in a water-hydrocarbon-containing mixture comprising:

a. a plurality of glass tubular containers for containing the water-hydrocarbon mixture, each of the tubular containers
      (1) having one open end and one closed end, and
      (2) comprised of a material not substantially electrically conductive;
   b. an aluminum heating block/electrode having a plurality of tubular recesses therein,
      (1) each of the tubular recesses for receipt of one of the tubular containers disposed closed-end down,
      (2) the heating block/electrode comprising a heat conducting and electrical current conducting material,
         (a) for conducting heat to the tubular containers, and
         (b) for applying an electrical potential across the water-hydrocarbon mixture;
   c. a mixing blade/electrode member disposed within each of the tubular containers
      (1) for mixing the water-hydrocarbon mixture with the chemical additive, and
      (2) for applying an electrical potential to the water-hydrocarbon mixture;
   d. a transformer means having two poles, an electrically active pole and a grounded pole, for applying an electrical potential to the two electrodes wherein;
      (1) one pole is connected to the mixing blade/electrode; and
      (2) one pole is connected to the heating block/electrode.
   e. a cover member for electrically connecting one pole of the transformer means to at least one of the mixing blade/electrode members, the cover member comprising:
      (1) a common plate member comprised of a substantially non-electrically conductive material;
      (2) having a plurality of electrical connecting means insulated from one another and disposed through apertures in the common plate member,
      (3) wherein one end portion of each of the electrical connecting means is in electrical connection with one pole of the transformer means; and
      (4) wherein an opposite end portion of each of the electrical connecting means is in electrical connection with a different one of the mixing blade/electrode members;
   f. wherein the cover member further comprises:
      (1) a plurality of cylindrical members having an open bottom portion;
      (2) and being fixedly attached at a top portion of the cylindrical members to the common plate member, wherein the opposite end portion of one of each of the electrical connecting means is disposed inside the top portion of one of the cylindrical members; and
      (3) wherein when the liquid is being heated, the tubular containers are positioned in the recesses in the heating block/electrode member and the cylindrical members are slid over a top end portion of the tubular containers.

2. The electrostatic coalescer testing apparatus according to claim 1, wherein the tubular containers comprise glass.

3. The electrostatic coalescer testing apparatus according to claim 2, wherein in the transformer means the electrically active pole is connected to the mixing blade/electrode and the grounded pole is connected to the heating block/electrode.

4. The electrostatic coalescer testing apparatus according to claim 1, wherein the heating block/electrode is aluminum.

5. The electrostatic coalescer testing apparatus according to claim 1, further comprising an explosion-resistant shield removably disposed over at least a portion of the heating block/electrode for safety protection in the case of an explosion of the tubular containers.

6. An electrostatic coalescer testing apparatus for testing the ability of chemical additives to facilitate electrostatic coalescence of water in a water-hydrocarbon-containing mixture comprising:

a. a plurality of tubular containers for containing the water-hydrocarbon mixture, each of the tubular containers
      (1) having one open end and one closed end, and
      (2) comprised of a material not substantially electrically conductive;
   b. a heating block/electrode having a plurality of tubular recesses therein,
      (1) each of the tubular recesses for receipt of one of the tubular containers disposed closed-end down,
      (2) the heating block/electrode comprising a heat conducting and electrical current conducting material,
         (a) for conducting heat to the tubular containers, and
         (b) for applying an electrical potential across the water-hydrocarbon mixture;
   c. a mixing blade/electrode member disposed within each of the tubular containers
      (1) for mixing the water-hydrocarbon mixture with the chemical additive, and
      (2) for applying an electrical potential to the water-hydrocarbon mixture;
   d. a transformer means having two poles for applying an electrical potential to the two electrodes wherein;
      (1) one pole is connected to the mixing blade/electrode; and
      (2) one pole is connected to the heating block/electrode.

7. The electrostatic coalescer testing apparatus according to claim 6, wherein the plurality of recesses in the heating block/electrode are all situated on the same side of the heating block/electrode.

8. The electrostatic coalescer testing apparatus according to claim 7, further comprising a plurality of transformer means for independently controlling the electrical potential applied to the water-hydrocarbon mixture in each of the tubular containers.

9. The electrostatic coalescer testing apparatus according to claim 6, wherein the heating block/electrode is at ground potential.

10. The electrostatic coalescer testing apparatus according to claim 6, further comprising a cover member for electrically connecting one pole of the transformer means to at least one of the mixing blade/electrode members, the cover member comprising:

a. a common plate member comprised of a substantially non-electrically conductive material;
   (1) having a plurality of electrical connecting means insulated from one another and disposed through apertures in the common plate member,
   (2) wherein one end portion of each of the electrical connecting means is in electrical connection with one pole of the transformer means; and
   (3) wherein an opposite end portion of each of the electrical connecting means is in electrical connection with a different one of the mixing blade/electrode members.

11. The electrostatic coalescer testing apparatus according to claim 10, wherein the cover member further comprises:
   a. a plurality of cylindrical members having an open bottom portion;
   b. and being fixedly attached at a top portion of the cylindrical members to the common plate member, wherein the opposite end portion of one of each of the electrical connecting means is disposed inside the top portion of one of the cylindrical members; and
   c. wherein when the liquid is being heated, the tubular containers are positioned in the recesses in the heating block/electrode member and the cylindrical members are slid over a top end portion of the tubular containers.

12. An electrostatic coalescer testing apparatus for testing the ability of chemical additives to facilitate electrostatic coalescence of water in a water-hydrocarbon-containing mixture comprising:
   a. a plurality of glass tubular containers for containing the water-hydrocarbon mixture, each of the tubular containers
      (1) having one open end and one closed end, and
      (2) comprised of a material not substantially electrically conductive;
   b. an aluminum heating block/electrode having a plurality of tubular recesses therein,
      (1) each of the tubular recesses for receipt of one of the tubular containers disposed closed-end down,
      (2) the heating block/electrode comprising a heat conducting and electrical current conducting material,
         (a) for conducting heat to the tubular containers, and
         (b) for applying an electrical potential across the water-hydrocarbon mixture;
   c. a mixing blade/electrode member disposed within each of the tubular containers
      (1) for mixing the water-hydrocarbon mixture with the chemical additive, and
      (2) for applying an electrical potential to the water-hydrocarbon mixture;
   d. a transformer means having two poles, an electrically active pole and a grounded pole, for applying an electrical potential to the two electrodes wherein;
      (1) one pole is connected to the mixing blade/electrode; and
      (2) one pole is connected to the heating block/electrode.
   e. a cover member for electrically connecting one pole of the transformer means to at least one of the mixing blade/electrode members, the cover member comprising:
      (1) a common plate member comprised of a substantially non-electrically conductive material;
      (2) having a plurality of electrical connecting means insulated from one another and disposed through apertures in the common plate member,
      (3) wherein one end portion of each of the electrical connecting means is in electrical connection with one pole of the transformer means; and
      (4) wherein an opposite end portion of each of the electrical connecting means is in electrical connection with a different one of the mixing blade/electrode members.

13. The electrostatic coalescer testing apparatus according to claim 12, wherein in the transformer means the electrically active pole is connected to the mixing blade/electrode and the grounded pole is connected to the heating block/electrode.

14. The electrostatic coalescer testing apparatus according to claim 13, further comprising a plurality of transformer means for independently controlling the electrical potential applied to the water-hydrocarbon mixture in each of the tubular containers.

15. The electrostatic coalescer testing apparatus according to claim 13, wherein the cover member the cover member further comprises:
   a. a plurality of cylindrical members having an open bottom portion;
   b. and being fixedly attached at a top portion of the cylindrical members to the common plate member, wherein the opposite end portion of one of each of the electrical connecting means is disposed inside the top portion of one of the cylindrical members; and
   c. wherein when the liquid is being heated, the tubular containers are positioned in the recesses in the heating block/electrode member and the cylindrical members are slid over a top end portion of the tubular containers.

16. The electrostatic coalescer testing apparatus according to claim 15, further comprising an explosion-resistant shield removably disposed over at least a top portion of the heating block/electrode for safety protection in the case of an explosion of the tubular containers.

* * * * *